United States Patent
Shinitzky et al.

(10) Patent No.: US 8,101,552 B2
(45) Date of Patent: Jan. 24, 2012

(54) CYCLIC PHOSPHATES AS PLANT GROWTH REGULATORS

(75) Inventors: Meir Shinitzky, Rehovot (IL); Dan Pelah, Omer (IL); David Mills, Beer Sheva (IL); Hanna Mills, legal representative, Beer Sheva (IL); Avishay Pelah, Savyon (IL)

(73) Assignees: Yeda Research and Development Company Ltd., Rehovat (IL); Ben Gurion University of the Negev Research and Development Authority, Beer Sheva (IL)

( * ) Notice: Subject to any disclaimer, the term of this patent is extended or adjusted under 35 U.S.C. 154(b) by 713 days.

(21) Appl. No.: 11/908,784

(22) PCT Filed: Mar. 14, 2006

(86) PCT No.: PCT/IL2006/000332
§ 371 (c)(1),
(2), (4) Date: Nov. 10, 2008

(87) PCT Pub. No.: WO2006/097924
PCT Pub. Date: Sep. 21, 2006

(65) Prior Publication Data
US 2009/0170701 A1   Jul. 2, 2009

Related U.S. Application Data

(60) Provisional application No. 60/661,022, filed on Mar. 14, 2005.

(51) Int. Cl.
*A01N 57/02* (2006.01)

(52) U.S. Cl. ................................ 504/127; 504/194

(58) Field of Classification Search ............ 504/127, 504/194
See application file for complete search history.

(56) References Cited

U.S. PATENT DOCUMENTS 3,008,976 A * 11/1961 Lorenz et al. ............... 558/183
6,495,532 B1 * 12/2002 Bathurst et al. ............. 514/110

OTHER PUBLICATIONS

Lorenz et al. (Accession No. 1961:17527 CAPLUS Document No. 55:17527, abstract of DE 1050331).*
Diop, Cheikh et al. Accession No. 1998:538964 CAPLUS, Document No. 129:286921, abstract of Journal de la Societe Ouest-Africaine de Chimie (1997), 2(4), 31-49.*

* cited by examiner

*Primary Examiner* — Sabiha Qazi
(74) *Attorney, Agent, or Firm* — Browdy and Neimark, PLLC

(57) ABSTRACT

The invention pertains to the use of six-membered cyclic phosphates as plant growth regulators and methods for regulating the growth of plants using such compounds.

15 Claims, 6 Drawing Sheets type of Cyclic Propanediol P

CYCLIC PHOSPHATES AS PLANT GROWTH REGULATORS

FIELD OF THE INVENTION

This invention relates to use of cyclic phosphates as plant growth regulators.

BACKGROUND OF THE INVENTION

Elements essential for metabolism of plants provide the power and building blocks, which are required for sustaining growth of plants and completion of life cycle. Such elements may be added to increase growth and yield. Another group of compounds, which also occur in nature, may be supplemented to plants in order to manipulate the growth and the development of the plant. This group is composed of plant growth regulators (PGR) or phytohormones also known as plant hormones. Since naturally occurring PGR are sensitive to ex situ breakdown and to metabolism in situ, they were frequently replaced by synthetic PGR for practical applications mostly in agriculture.

Plant hormones play a crucial role in controlling the way which plants grow and develop. While metabolism provides the power and building blocks for plant life, it is the hormones that regulate the speed of growth of the individual parts and integrate these parts to produce the form that we recognize as a plant, e.g. the branching of the plants. In the plant world several classes of hormones are of major importance {for general literature see: (a) Davis P J, ed., 'Plant Hormones' Physiology, Biochemistry and Molecular Biology, Kluwer Academic Publishers, Dordrecht, Boston, London, 1995; (b) George E F, Plant Propagation by Tissue Culture. Part 1, The Technology; Part 2, In practice, Exegetics Ltd., Edington, 1993, 1995; (c) Basra A. S. ed, Plant Growth regulators in Agriculture and Horticulture. Food products Press. New York 2000; and (d) Taiz L. and Ziegler E. Plant Physiology $3^{rd}$ edition. Sinauer Associates Inc Publisher. Sunderland, Mass.}:

Auxins such as indole-3-acetic acid (IAA), indole-3-butyric acid (IBA), 1-naplhtlhaleneacetic acid (NAA) and 2,4-dichlorophenoxyacetic acid (2,4-D) affect mainly cell division and enlargement and stem growth, vascular tissue differentiation in phloem and xylem, root initiation and callus formation.

Cytokinins such as zeatin (Z), 6-benzylaminopurine (BAP) and kinetin affect mainly adventitious shoot formation, cell division and inhibition of root formation.

Gibberellins such as gibberellic acid (GA3), gibberellin 1 (GA1), gibberellin 4 (GA4) affect mainly stem growth, bolting in long day plants and release from dormancy in seeds, somatic embryos, apical buds and bulbs.

Ethylenes have an effect on shoot and root growth and differentiation, root formation, abscission of leaves and roots, flower and leaf senescence and fruit ripening.

Abscisic acids have an effect on stomata closure, inhibition of shoot growth, induction of seed dormancy and production of storage protein.

In recent years more substances, e.g. brassinolides, jasmonic acid and salicylic acid were recognized as plant growth regulators.

In respect to the effect of plant hormones solely on plant development, the most important are the stimulation of auxin and gibberllins on cell elongation and differentiation, the effect of cytokinin, auxin and gibberllins on cell division, and the effect of both auxins and cytokinins on organ differentiation.

Plant hormones have commercial value in agriculture and horticulture. A limited list of applications related to growth stimulation include enhancement of the size of seedless grapes by GA, development of partenocarpic fruits by auxin, root induction in plant propagation by auxins.

One other group of plant growth regulators known as triazoles has a pronounced effect of stress protection. These compounds inhibit GA biosynthesis and also affect the level of other hormones as ABA, cytokinin and ethylene. Triazole-treated plants use less water and have increased tolerance to drought mainly due to reduced transpiration caused by decreased leaf area and increased epicuticular wax accumulation. Under conditions of water deficiency, triazoles have an increased effect on the growth of plants. Triazoles also increase tolerance of plants to chilling and freezing temperatures, to high temperature stress and to air pollutants such as $SO_2$ and $O_3$.

SUMMARY OF THE INVENTION

The present invention is based on the fact that certain cyclic phosphates may be used as efficient plant growth regulators enhancing plant branching growth, direct organogenesis and root growth.

Thus the invention is directed to a composition for regulating growth of plants comprising an effective amount of a compound of formula (I)

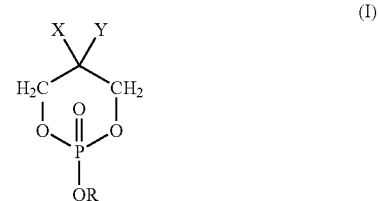

or its salts;
wherein X is hydrogen, $C_{1-4}$, $C_{1-4}O—$, $NO_2$ or $NH_2$; Y is hydrogen, $C_{1-4}$, $C_{1-4}O—$, or $CH_2OH$; R is hydrogen, $C_{1-6}$allyl or $C_{1-6}C(=O)—$; and the salts are selected from ammonium, sodium, calcium, potassium, sulfonate, sulfate, phosphoric, phosphonic.

Preferably the compounds are selected from compounds of formula (I) wherein X is hydrogen, $NH_2$ or $NO_2$, Y is hydrogen or $CH_2OH$, R is hydrogen or $C_{1-6}$alkyl, preferably $C_{1-4}$, and their sodium or sulfate salts. In particular, the compounds are selected from:

X, Y and R are hydrogen, or its sodium or sulfate salt;

X is $NO_2$, Y is $CH_2OH$ and R is hydrogen, or its sodium salt or sulfate salt;

X is $NH_2$, Y is $CH_2OH$ and R is hydrogen, or its sodium salt or sulfate salt;

X is $NH_2$, Y is $CH_2OH$ and R is hydrogen, or its sodium salt or sulfate salt;

X and Y are hydrogen and R is $C_{1-6}$alkyl, or its sodium or sulfate salt;

X is $NO_2$, Y is $CH_2OH$ and R is $C_{1-6}$alkyl, or its sodium salt or sulfate salt;

X is $NH_2$, Y is $CH_2OH$ and R is $C_{1-6}$alkyl, or its sodium salt or sulfate salt;

X is $NH_2$, Y is $CH_2OH$ and R is $C_{1-6}$alkyl, or its sodium salt or sulfate salt.

The composition may be solid, liquid or in gel form. In case of a liquid or gel form, the amount of the compound of formula (I) is from about 0.1 to about 200 µM, preferably from about 1 to about 100 µM and most preferably from about 10 to about 100 µM.

The composition may further comprise an additional synthetic or naturally occurring plant growth regulator selected from the group consisting of Auxins, Cytokinins, Gibberellins, Ethylenes, Abscisic acid, brassinolides, jasmonic acid and salicylic acid.

The invention is further directed to a method for regulating the growth of plants and optionally enhancing plant branching growth, direct organogenesis and root growth. The method comprises the application to the plant or its vicinity of an effective amount of a compound of formula (I) or its salts. The method may comprise the application of a compound of formula (I) or its salts either alone or in combination with additional synthetic or naturally occurring plant growth regulator selected from the group consisting of Auxins, Cytokinins, Gibberellins, Ethylene Abscisic acid, brassinolides, jasmonic acid and salicylic acid.

The regulation according to the present invention is selected from increase the growth of roots, buds, seeds, flowers, leaves and fruit, modulate the formation of metabolites, enhancement or the slowing of flowering, ripening of fruit or increasing the number of growing cycles.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF EXEMPLARY EMBODIMENTS

Figure 1:
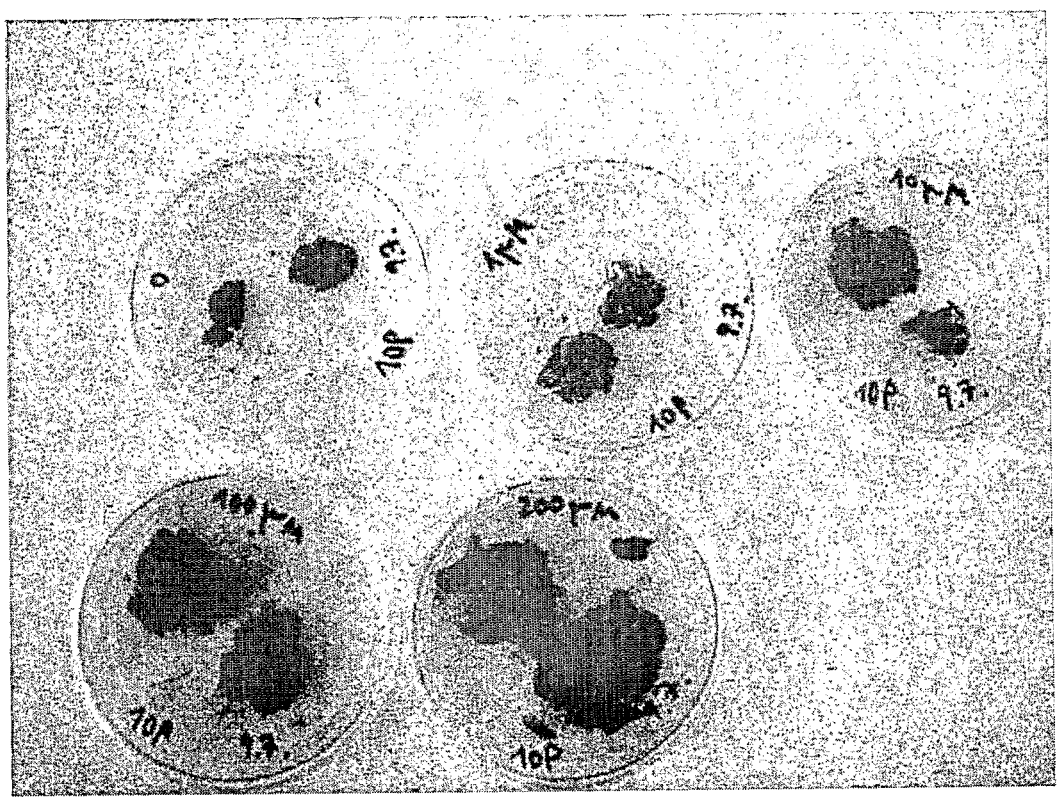
FIG. 1 shows the effect of 1,3 cyclic propandiol phosphate (cPP) having M.W. 235 (designated 3) as a plant growth regulator compared to DL-α-glycerophosphate.

Plant hormones are essential for controlling the way which plants grow and develop. These hormones regulate the rate of growth of each individual part of the plant and further the integration of all the individual parts to produce the end result, which is the form of the particular plant. The present invention discloses a new family of plant growth regulators (PGR) which may be used alone or in combination with other known PGR. The new family comprises six membered cyclic phosphates, which were found to be efficient plant growth regulators and may thus substitute known plant growth regulators commonly used in agriculture. The PGRs of the present invention enable the control of growth of specific desired parts of the plant and of plant components and ingredients. For example it is possible to control with the new PGRs of the present invention and increase the growth of roots, buds, seeds, flowers, leaves and fruit. The regulation of the plant growth agent may further shorten or extend, hold back or increase certain stages in the development of the plants. Such regulation may amount to enhancement or the slowing of flowering, ripening of fruit or increasing the number of growing cycles. Furthermore, due to the fact that the plant growth regulators of the present invention, without being bound to any mechanism or theory, interfere with the plant metabolism by promoting or inhibiting vegetative and/or generative growth, various metabolites such as protein and/or carbohydrates produced by the plants may be controlled, increased or decreased. The plant growth regulators of the present invention may further cause a reduction in the amount of required irrigation. As a result of the use of the plant regulators of the present invention the frequency of required irrigation as well as the amount of water used in each irrigation cycle may be reduced. Thus plants may be grown in locations where previously it was not possible to grow such plants due to economical reasons or to lack of sufficient irrigation resources.

The amount of active compound applied varies as a function of the nature of the plant, the nature of the desired activity and the climate. Typically the amount of active PGR in a liquid or gel formulation is from about 0.1 µM to about 200 µM, preferably from about 1 µM to about 100 µM and most preferably from about 10 µM to about 100 µM. A particular formulation may contain in addition to the active PGR, auxiliaries and adjuvants which may further affect the amount of the active component. The final plant growth formulation may be an aqueous or a non-aqueous formulation with appropriate surfactant, alcohol, detergent or emulsifier. The surfactants can be any of the well-known anionic, cationic or non-ionic surfactants such as organosilicone. Emulsifiers may be chosen from mineral oils, ethoxylated alcohols, quartenary surfactants, sulfonates, alkanolamides or fatty acids. Mineral oils are known to prevent enhanced evaporation of spray droplets when the composition is applied as a spray. Additional oils which may be used are coconuts, citrus, soybeans and peanuts, citronella and neem oils.

The composition may be in any commercial form such as spray, granules, tablets, dispersible powders, liquid or solid concentrates. It may be formulated as a slow release formulation, e.g. in zeolites. The formulation may further comprise wax serving as an effective penetrating and adhesive agent when applied to the plant's surfaces. Such a composition will form a waxy coat on the plant's surface which is not easily removed by irrigation or rain. The wax may be a petroleum wax, natural wax, water or alcohol soluble synthetic waxes, e.g. acrylic polymers acrylic copolymers or styrene acrylic copolymers). Since some waxes are not readily soluble, it may be necessary to use a solvent in cases of water insoluble waxes.

Additionally, the plant growth regulators of the present invention may comprise the six membered cyclic phosphates of the present invention in combination with commercially well known and well used plant growth regulators to produce a composition which effects plant growth rate. Non limiting examples of such plant growth regulators are naturally-occurring plant hormones such as indol-3-ylacetic acid, or their synthetic analogues such as 4-indol-3-ylbutyric acid, Auxins, Cytokinins (e.g. kinetin, cytokinin, dihydrozeatin, zeatin), Gibberellins, Ethylenes, Abscisic acid, brassinolides, jasmonic acid and salicylic acid. Such a combination comprising at least two plant regulators may be a synergistic composition comprising altogether a smaller amount of each plant regulator, thus reducing the amount of active material.

Figure 2A:
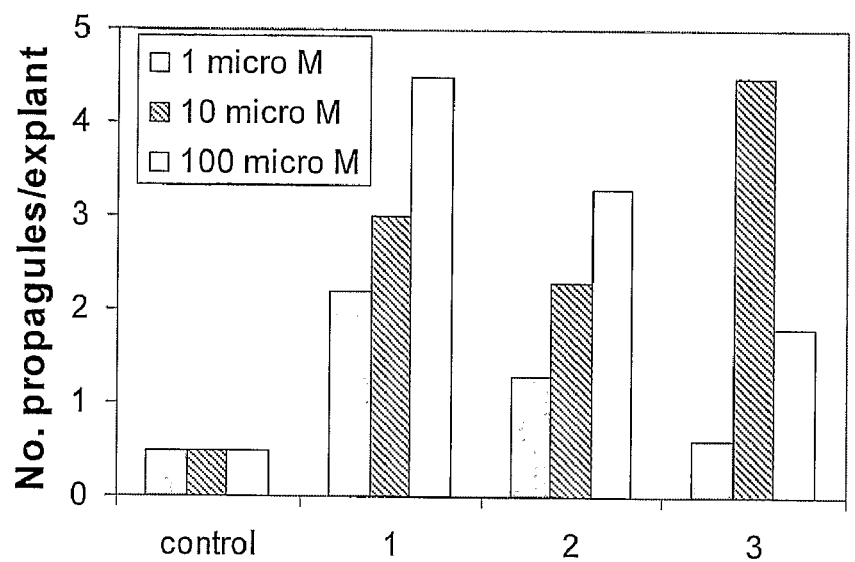
FIG. 2 gives a quantitative measure for the effect on the (A) number of plantlets (propagules) regeneration on the original mature leaf (explant) and the (B) increased obtained biomass after treatment with three 1,3 cyclic propandiol phosphate, designated 1, 2 and 3 having M.W. of 160, 213 and 235, respectively.
Figure 2B:
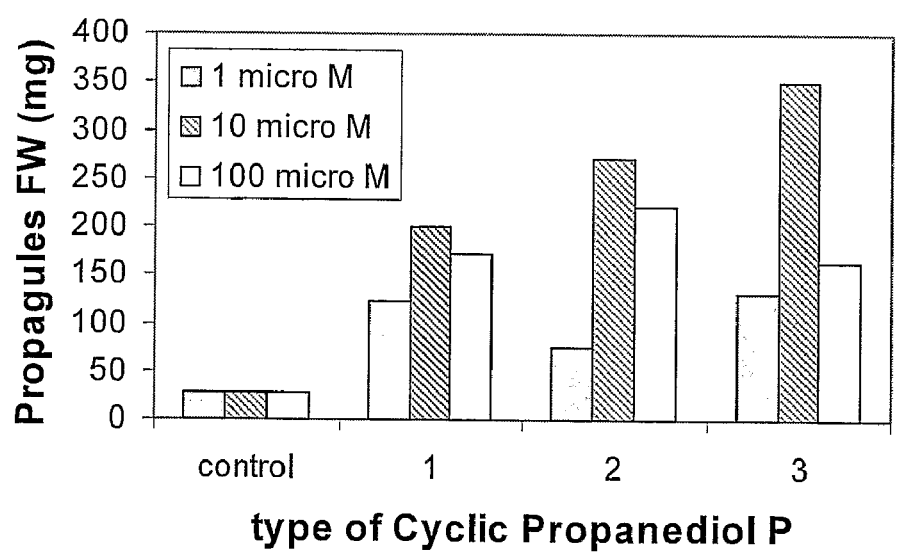
Figure 3A:
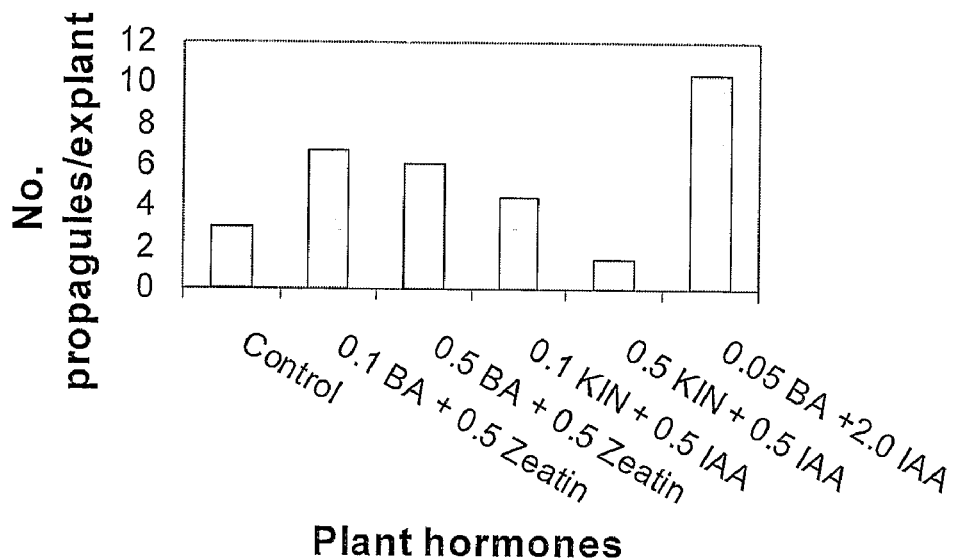
FIG. 3 gives a quantitative measure for the effect on the (A) number of plantlets (propagules) regeneration on the original mature leaf (explant) and the (B) increased obtained biomass after treatment with known plant growth regulators.
Figure 3B:
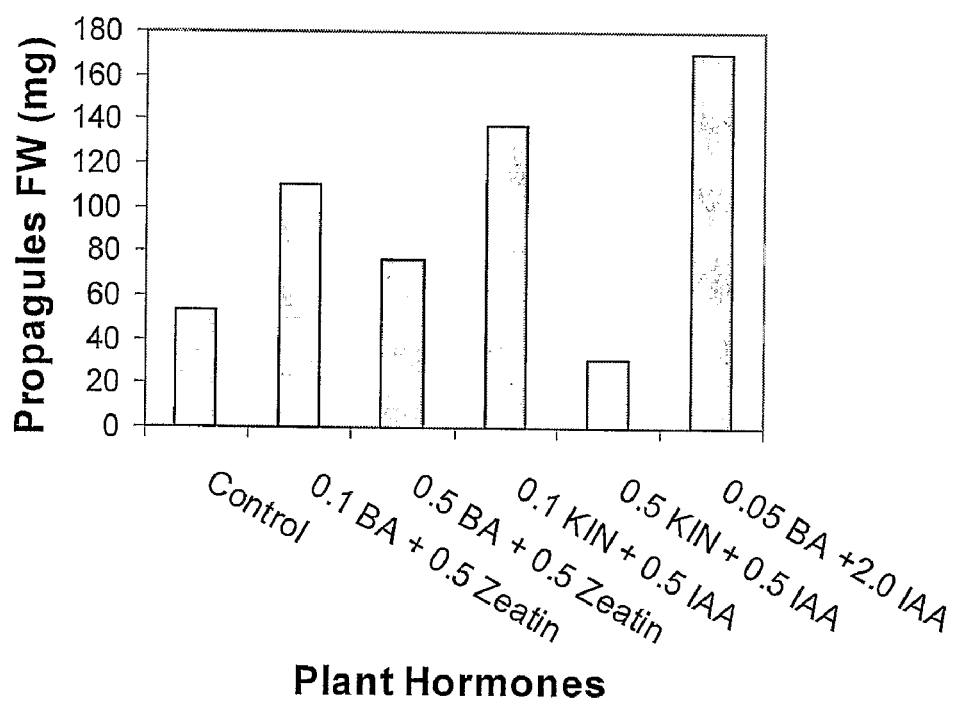

The six membered cyclic phosphates of the present invention and in particular, [1,3,2]Dioxaphosphinan-2-ol, its sodium salt, i.e. sodium-[1,3,2]-dioxaphosphinan-2-olate, 5-Amino-5-hydroxymethyl-[1,3,2]dioxaphosphinan-2-ol and 5-Hydroxymethyl-5-nitro-[1,3,2]dioxaphosphinan-2-ol and their sodium salts were found to be very efficient plant growth regulators in enhancing the growth of plants relative to plant grown in the presence of a control and/or enhancing plant branching growth and direct organogenesis. The control used was the linear DL-α-glycerophosphate which is the non cyclic moiety analog of the six membered ring. In particular, the addition of sodium-[1,3,2]-dioxaphosphinan-2-olate (M.W. of 160, hereinafter 1), 5-Hydroxymethyl-5-nitro-[1,3,2]dioxaphosphinan-2-ol (M.W. of 213, hereinafter 2) and its sodium salt, i.e. sodium-5-Hydroxymethyl-5-nitro-[1,3,2]dioxaphosphinan-2-olate (M.W. 235, hereinafter 3) had an effect on direct organogenesis, stimulation of cells in the leaf to divide and form meristems that eventually form new plantlets. FIGS. 2A and 2B demonstrate the effect compounds 1, 2 or 3 had on the increase of the number (FIG. 2A) and the biomass (FIG. 2B) of propagules developed on a leaf of African violet during a two-month treatment. The effect obtained by the new family of PGR of the present invention may compared to the increase in the number and of the biomass of propagules developed on a leaf of African Violet during a two-month treatment with know Auxins and cytokinins shown in FIGS. 3A and 3B, respectively. Furthermore, the application of a six-membered ring phosphate of the present invention on excised leafs produced an effect of the development of shoots and roots. A similar effect was achieved with plant callus, where the application of the six-membered rings plant growth regulators of the invention on callus prepared from roots caused the callus to survive and grow under light where applying the control compound resulted in the death of the callus.

Figure 6A:
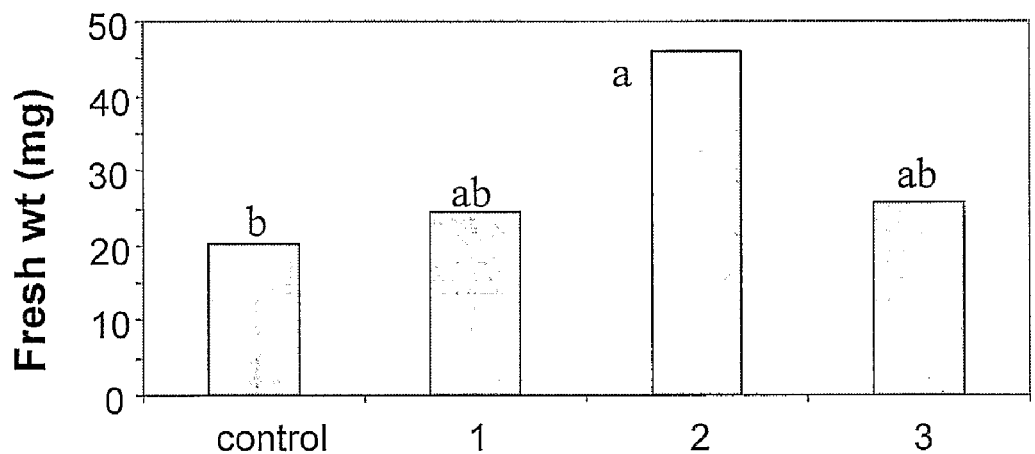
FIG. 6 gives a quantitative measure for the effect on the (A) increase of biomass of Rubia roots and the (13) growth rate after treatment with three 1,3 cyclic propandiol phosphate, designated 1, 2 and 3 having M.W. of 160, 213 and 235, respectively.
Figure 6B:
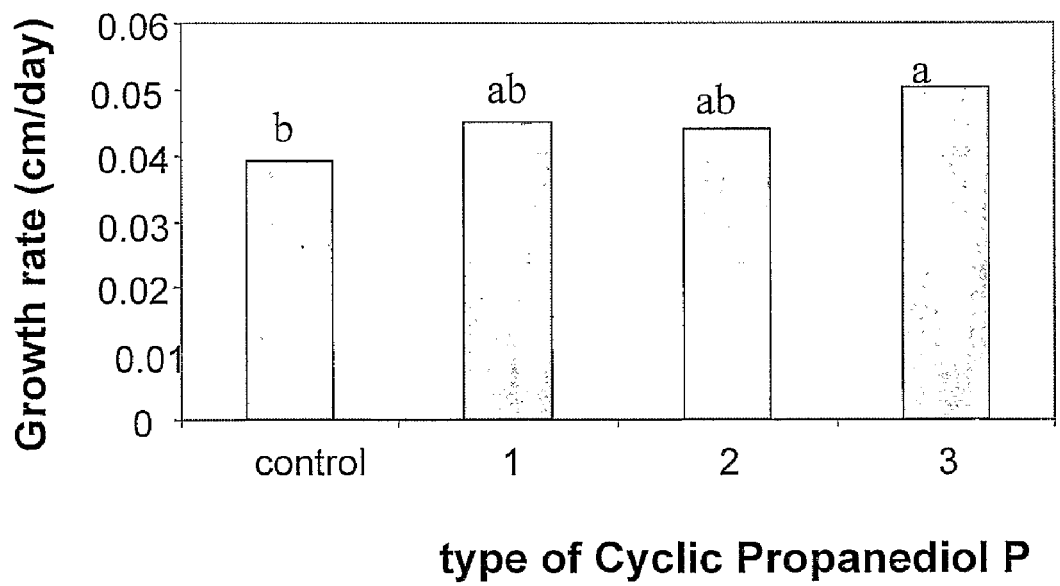

Still yet the application of the six-membered ring phosphate of the present invention caused root elongation under darkness. Rubia roots (clone R4C) were grown routinely in liquid N5 medium on a shaker then roots were transferred to solid MS plus 1 μM of either 5-Hydroxymethyl-5-nitro-[1,3,2]dioxaphosphinan-2-ol or the sodium-5-Hydroxymethyl-5-nitro-[1,3,2]dioxaphosphinan-2-olate under light (1 inflorescent bulb) or darkness. FIG. 6 demonstrates that under darkness, these two PGR stimulated biomass accumulation (6A) and growth rate (6B) of Rubia roots, respectively. These positive effects were not observed under light.

EXAMPLES

Example 1

Plantlets of African violet and transformed callus of Rubia tinctorum were grown and subcultured on a rich medium that included macronutrients, micronutrients, vitamines and sugar as a source of carbohydrates according to Murashige, T. and F. Skoog. 1962. Physiol. Plant 15:473-497. No plant growth regulators were added. The nutrients were dissolved in agar-agar, the medium was adjusted to pH of 5.8 and autoclaved for 20 min at a temperature of 121° C. DL-α-Glycerophosphate (αGP) or 1,3 cyclic propanediol phosphate (1,3 cPP) were added to the medium after filtration to yield a series of 0, 1, 10, 100 or 200 μM of 1,3 cPP and of 200 μM of DL-α-Glycerophosphate.

Pieces of callus or small leaves that were excised from the plantlets were then placed on the solid medium described above.

In the media which included 1,3 cPP shoots and roots developed from the leaf base of African violet to form a new plantlet or a cluster of new plantlets that could be excised and keep growing individually. This growth pattern occurred with no presence of plant growth regulators. In the case of αGP or without any additives no such growth was observed. 1,3 cPP had a marked effect on growth of plantlets from leaf base. More plantlets were developed with bigger leaflets and longer roots. The entire cluster accumulated more biomass with the increase in 1,3 cPP concentration being 124, 228, 470, 412, 541 mg FW for 0, 1, 10, 100 and 200 μM of 1,3 cPP, respectively, after 8 weeks (FIG. 1). In another experiment, leaves were exposed to αGP and to 1,3 cPP, both in concentration of 0 and 200 μM. After 4 weeks it was clear that 1,3 cPP had an effect on plantlet growth while αGP had only an insignificant effect on enhancement of plant growth.

Example 2

In an analogues experiment the effect of 1,3cPP on transformed callus of Rubia tinctorum was tested. The callus was prepared from roots that initially were produced after infecting the leaves of the species with Agrobacterium fhizogenes that caused a natural transformation. The callus is light sensitive and should be grown in darkness.

Figure 4:
FIG. 4 shows the effect of 1,3 cyclic propandiol phosphate (M.W. 235, 3), which enables a light sensitive callus to survive and further grow under light.

Under light the callus in the control did not survive. In these conditions 1,3cPP at the various concentrations had a dramatic effect of allowing the callus to survive and grow under light (FIG. 4).

Example 3

Figure 5:
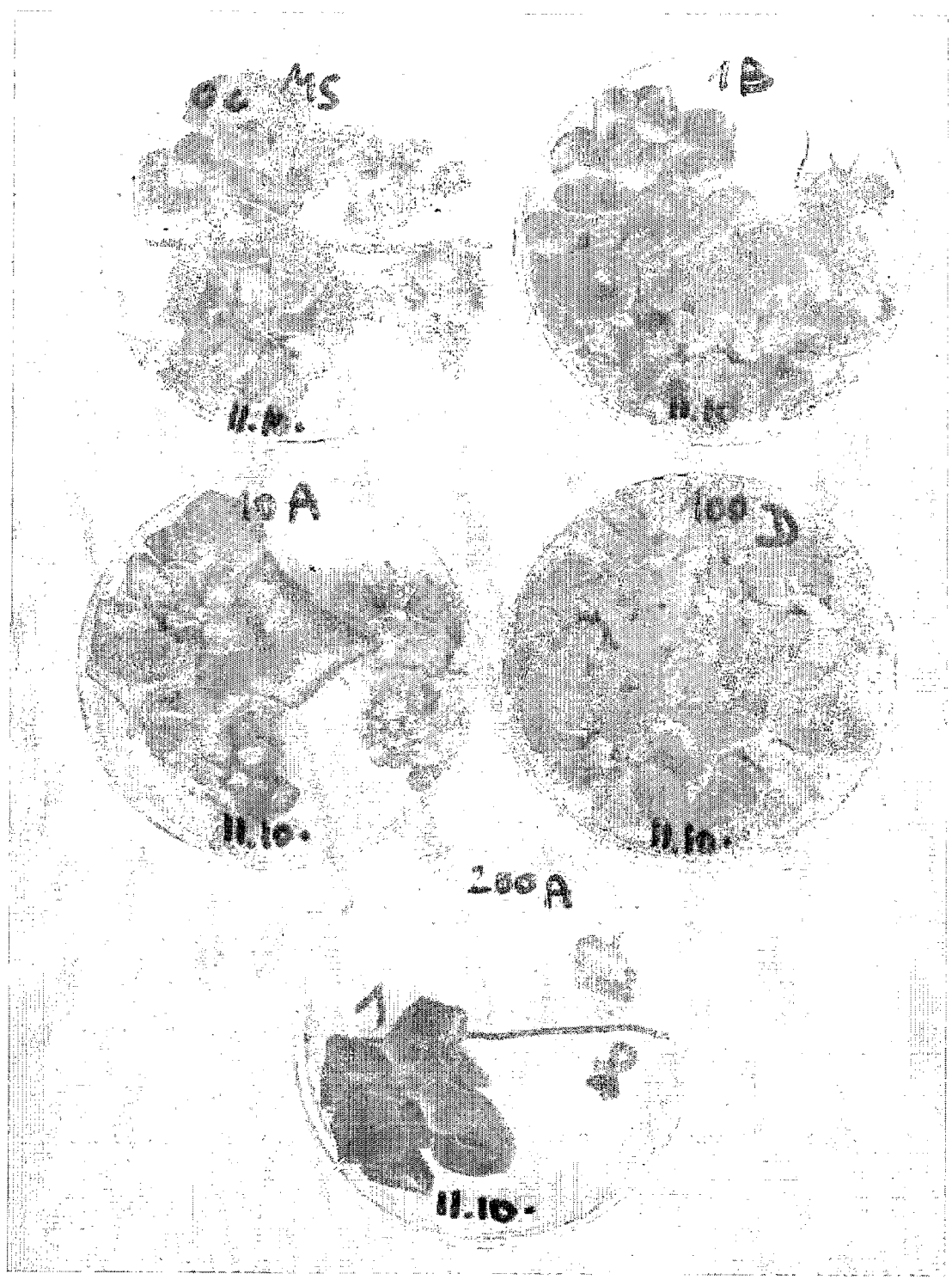
FIG. 5 shows the effect of 1,3 cyclic propandiol phosphate on the organogenesis of the house plant *Saintpaulia ionantha*.

Cut leafs of the houseplant Saintpaulia ionantha was immersed with MS-medium to which were added in several separate test tubes 0 (no additive), 1, 10, 100, and 200 micromolar 1,3 cyclic propanediol phosphate (MW of 235) for 2 successive cultures each of 2 months (two transfers to the same composition of medium). FIG. 5 demonstrates that the addition of the compound is beneficial for enhancing the effect of recuperation of propagules from leaf cuttings over to the effect achieved with the common procedure (leaf cutting inserted in a MS in a test-tube). An application of 100 μM, was most beneficial. The numbers of plantlets produced per original leaf cutting were 4.4, 6.5, 4, 8.5 and 0.5, respectively for the addition of 0, 1, 10, 100 and 200 μM. 200 μM is apparently deleterious for organogenesis.

The invention claimed is:
1. A plant growth regulator composition comprising an amount effective for regulating growth of plants of a compound of formula (I) or its salts

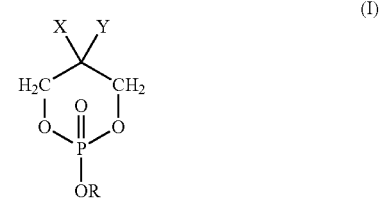

wherein X is hydrogen, $C_{1-4}$, $C_{1-4}O-$, $NO_2$ or $NH_2$; Y is hydrogen, $C_{1-4}$, $C_{1-4}O-$, or $CH_2OH$; R is hydrogen, $C_{1-6}$alkyl or $C_{1-6}C(=O)-$; and the salts are selected from ammonium, sodium, calcium, potassium, sulfonate, sulfate, phosphoric, phosphonic.

2. A plant growth regulator composition according to claim 1 wherein X is hydrogen or $NO_2$, Y is hydrogen or $CH_2OH$, R is hydrogen or $C_{1-6}$alkyl.

3. A plant growth regulator composition according to claim 1, wherein the compound is selected from:
- X, Y and R are hydrogen or its sodium salt or sulfate salt;
- X is $NO_2$, Y is $CH_2OH$ and R is hydrogen or its sodium salt or sulfate salt;
- X is $NH_2$, Y is $CH_2OH$ and R is hydrogen or its sodium salt or sulfate salt;
- X is $NH_2$, Y is $CH_2OH$ and R is hydrogen or its sodium salt or sulfate salt;
- X and Y are hydrogen and R is $C_{1-6}$alkyl, or its sodium or sulfate salt;
- X is $NO_2$, Y is $CH_2OH$ and R is $C_{1-6}$alkyl, or its sodium salt or sulfate salt;
- X is $NH_2$, Y is $CH_2OH$ and R is $C_{1-6}$alkyl, or its sodium salt or sulfate salt;
- X is $NH_2$, Y is $CH_2OH$ and R is $C_{1-6}$alkyl, or its sodium salt or sulfate salt.

4. A liquid or gel composition according to claim 1 wherein the amount of the compound of formula (I) is from about 0.1 to about 200 μM.

5. A plant growth regulator composition according to claim 1 further comprising an additional plant growth regulator.

6. A plant growth regulator composition according to claim 5 wherein said additional plant growth regulator is selected from the group consisting of Auxins, Cytokinins, Gibberellins, Ethylenes, Abscisic acid, brassinolides, jasmonic acid and salicylic acid.

7. A method for regulating the growth of plant comprising the application of an amount effective for regulating growth of plants of a compound of formula (I) or its salts to the plant or to its near vicinity

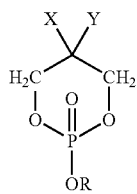
(I)

wherein X is hydrogen, $C_{1-4}$, $C_{1-4}O-$, $NO_2$ or $NH_2$; Y is hydrogen, $C_{1-4}$, $C_{1-4}O-$, or $CH_2OH$; R is hydrogen, $C_{1-6}$alkyl or $C_{1-6}C(=O)-$; and the salts are selected from ammonium, sodium, calcium, potassium, sulfonate, sulfate, phosphoric, phosphonic.

8. A method according to claim 7 wherein X is hydrogen or $NO_2$, Y is hydrogen or $CH_2OH$, R is hydrogen or $C_{1-6}$alkyl.

9. A method according to claim 7, wherein the compound is selected from:
- X, Y and R are hydrogen or its sodium salt or sulfate salt;
- X is $NO_2$, Y is $CH_2OH$ and R is hydrogen or its sodium salt or sulfate salt;
- X is $NH_2$, Y is $CH_2OH$ and R is hydrogen or its sodium salt or sulfate salt;
- X is $NH_2$, Y is $CH_2OH$ and R is hydrogen or its sodium salt or sulfate salt;
- X and Y are hydrogen and R is $C_{1-6}$alkyl, or its sodium or sulfate salt;
- X is $NO_2$, Y is $CH_2OH$ and R is $C_{1-6}$alkyl, or its sodium salt or sulfate salt;
- X is $NH_2$, Y is $CH_2OH$ and R is $C_{1-6}$alkyl, or its sodium salt or sulfate salt;
- X is $NH_2$, Y is $CH_2OH$ and R is $C_{1-6}$alkyl, or its sodium salt or sulfate salt.

10. A method according to claim 7 further comprising an additional plant growth regulator.

11. A method according to claim 10 wherein said additional plant growth regulator is selected from the group consisting of Auxins, Cytokinins, Gibberellins, Ethylenes, Abscisic acid, brassinolides, jasmonic acid and salicylic acid.

12. A method according to claim 7 wherein said regulation is selected from increase the growth of roots, buds, seeds, flowers, leaves and fruit, enhancement or slowing of flowering, ripening of fruit, or increasing the number of growing cycles.

13. A plant growth regulator composition according to claim 1, wherein said amount is no more than about 100 μM.

14. The composition of claim 4 wherein the amount of the compound Formula (I) is from about 1 to about 100 μM.

15. The composition of claim 4 wherein the amount of the compound Formula (I) is from about 10 to about 100 μM.

* * * * *